United States Patent
Maclean et al.

(10) Patent No.: US 8,607,972 B2
(45) Date of Patent: Dec. 17, 2013

(54) MISCARRIAGE CARE PACKAGE

(76) Inventors: Sandra M. Maclean, Wayzata, MN (US); Elizabeth Levang, Maple Plain, MN (US)

(*) Notice: Subject to any disclaimer, the term of this patent is extended or adjusted under 35 U.S.C. 154(b) by 1110 days.

(21) Appl. No.: 10/664,236

(22) Filed: Sep. 17, 2003

(65) Prior Publication Data

US 2004/0088839 A1 May 13, 2004

Related U.S. Application Data

(60) Provisional application No. 60/411,737, filed on Sep. 18, 2002.

(51) Int. Cl.
*B65D 69/00* (2006.01)

(52) U.S. Cl.
USPC .......................................... 206/223; 206/581

(58) Field of Classification Search
USPC ........................................................ 206/223
See application file for complete search history.

(56) References Cited

U.S. PATENT DOCUMENTS

| | | | | |
|---|---|---|---|---|
| 4,205,869 A | * | 6/1980 | Mathis | 294/1.3 |
| 4,702,378 A | * | 10/1987 | Finkel et al. | 206/581 |
| 4,917,238 A | * | 4/1990 | Schumacher | 206/223 |
| 5,244,096 A | * | 9/1993 | Stoner | 206/581 |
| 5,261,531 A | * | 11/1993 | Nieves | 206/581 |
| 5,454,797 A | | 10/1995 | Haswell | |
| 5,515,974 A | * | 5/1996 | Higson | 206/570 |
| 5,792,125 A | | 8/1998 | Webb | |
| 5,931,304 A | | 8/1999 | Hammond | |
| 6,012,586 A | * | 1/2000 | Misra | 206/571 |
| 6,434,762 B2 | * | 8/2002 | Gordon | 4/483 |
| 6,579,271 B1 | * | 6/2003 | Aruffo et al. | 604/355 |
| 2001/0032712 A1 | * | 10/2001 | Friedbauer et al. | 162/109 |
| 2003/0012701 A1 | * | 1/2003 | Sangha et al. | 422/102 |
| 2003/0136704 A1 | * | 7/2003 | Burgess | 206/581 |

FOREIGN PATENT DOCUMENTS

DE 168244 C 4/1906

\* cited by examiner

*Primary Examiner* — Lynne Anderson
(74) *Attorney, Agent, or Firm* — Stuart R. Hemphill; Dorsey & Whitney LLP (57) ABSTRACT

The present invention is a miscarriage kit. More specifically, the present invention is a kit for use with a miscarriage by a human. The kit comprises at least one item for use in helping the human with the miscarriage. For example, the miscarriage kit may contain at least one under pad/bed liner, at least one sanitary napkin, at least one towel, at least one pair of gloves, at least one specimen pan, and at last one container for holding pregnancy remains.

17 Claims, 7 Drawing Sheets

MISCARRIAGE CARE PACKAGE

CROSS-REFERENCE TO RELATED APPLICATION

The present application claims priority to U.S. provisional patent application 60/411,737, filed Sep. 18, 2002.

BACKGROUND OF THE INVENTION

The present invention relates to medical supplies and means and methods of treating and preparing a medical patient. More specifically, the present invention relates to obstetric supplies and obstetric means and methods of treating and preparing an obstetric patient.

A miscarriage is the cessation of a pregnancy before the fetus can survive and is defined as occurring before the twentieth week of gestation. The etiology is typically due to multiple factors and quite complex. Statistically speaking, one in four pregnancies end in miscarriage. In large part this high number is the result of the efficiency of the human reproductive system in screening out chromosomal abnormalities. Other reasons for miscarriages include: uterine or cervical defects; systemic maternal disorders; infectious diseases; hormonal deficiencies; blood group incompatibility; maternal age; injury; and environmental or industrial toxins.

A miscarriage that occurs in the early weeks of pregnancy may physically feel like heavy menstruation. It may include cramp-like sensations in the lower abdomen and be preceded by several days of blood spotting. Miscarriages that occur later will be of more intensity and include several days of vaginal bleeding, low back pain, abdominal cramping, and uterine contractions.

When a miscarriage is imminent (termed an inevitable abortion), vaginal bleeding and pain increase in intensity and the cervix begins to dilate. The fetus, amniotic sac and placenta, along with additional blood, are expelled from the uterus. This process typically lasts several hours or can occur over several days.

In an incomplete miscarriage, placental tissue remains in the uterus and removal is accomplished by a dilation and curettage (D&C). In this medical procedure, the cervix is dilated and the uterus scraped for any remaining tissue. Persistent vaginal bleeding evidences an incomplete miscarriage.

The woman may be asked by her physician to collect the fetus and tissue. These must be preserved and brought to a hospital or clinic for diagnostic examination by a pathologist. Once examined, the fetal remains can be transferred to a funeral home in preparation for a funeral or memorial service.

A woman and her partner may choose to collect fetal or pregnancy remains for later burial and/or ceremony. For many, this will help bring closure and assist in the grieving process.

A miscarriage is a traumatic event. The sight of blood, the intensity of physical pain, and the knowledge that one's baby has died can result in clinical shock. Not only is a miscarriage frightening, it is also emotionally overwhelming. Grief and mourning are a normal response to pregnancy loss. The incidence of clinical depression in women who have experienced a miscarriage is reported to be 85%.

Traditionally, the medical community has done a poor job of preparing a woman for a miscarriage. This has had the effect of needlessly magnifying a woman's suffering in an already physically and emotionally painful event.

There is a need in the art for a means of preparing a woman, her partner, and/or caregiver for a miscarriage and for caring for the woman. Also, there is a need in the art for a method of preparing a woman, her partner, and/or caregiver for a miscarriage and for caring for the woman. The miscarriage kit or package will assist medical personnel in providing instruction and care to their patients.

BRIEF SUMMARY OF THE INVENTION

The present invention, in one embodiment, is a miscarriage kit or package. More specifically, the present invention, in one embodiment, is a kit for use with a miscarriage by a human. The kit comprises at least one item for use in helping the human and/or caregiver with the miscarriage. For example, in one embodiment, the miscarriage kit may comprise at least one under pad/bed liner, at least one sanitary napkin, at least one towel, at least one pair of gloves, at least one specimen pan, and at least one container for holding pregnancy remains.

The present invention, in another embodiment, is a method of dealing with a miscarriage. One it has been determined that a pregnancy is ending, likely to end, or has ended in miscarriage, the method comprises facilitating a woman's access to items that will assist her and/or her caregiver in dealing with her miscarriage. In one embodiment, the act of facilitation is achieved by providing the woman and/or caregiver with a miscarriage kit including the items. In another embodiment, the actual facilitation is achieved by providing the woman and/or caregiver with a list reciting the items. The list is then used as a guide in obtaining some or all of the items recited on the list.

While multiple embodiments are disclosed, still other embodiments of the present invention will become apparent to those skilled in the art from the following detailed description, which shows and describes illustrative embodiments of the invention. As will be realized, the invention is capable of modifications in various obvious aspects, all without departing from the spirit and scope of the present invention. Accordingly, the drawings and detailed description are to be regarded as illustrative in nature and not restrictive.

DETAILED DESCRIPTION

Figure 1A:
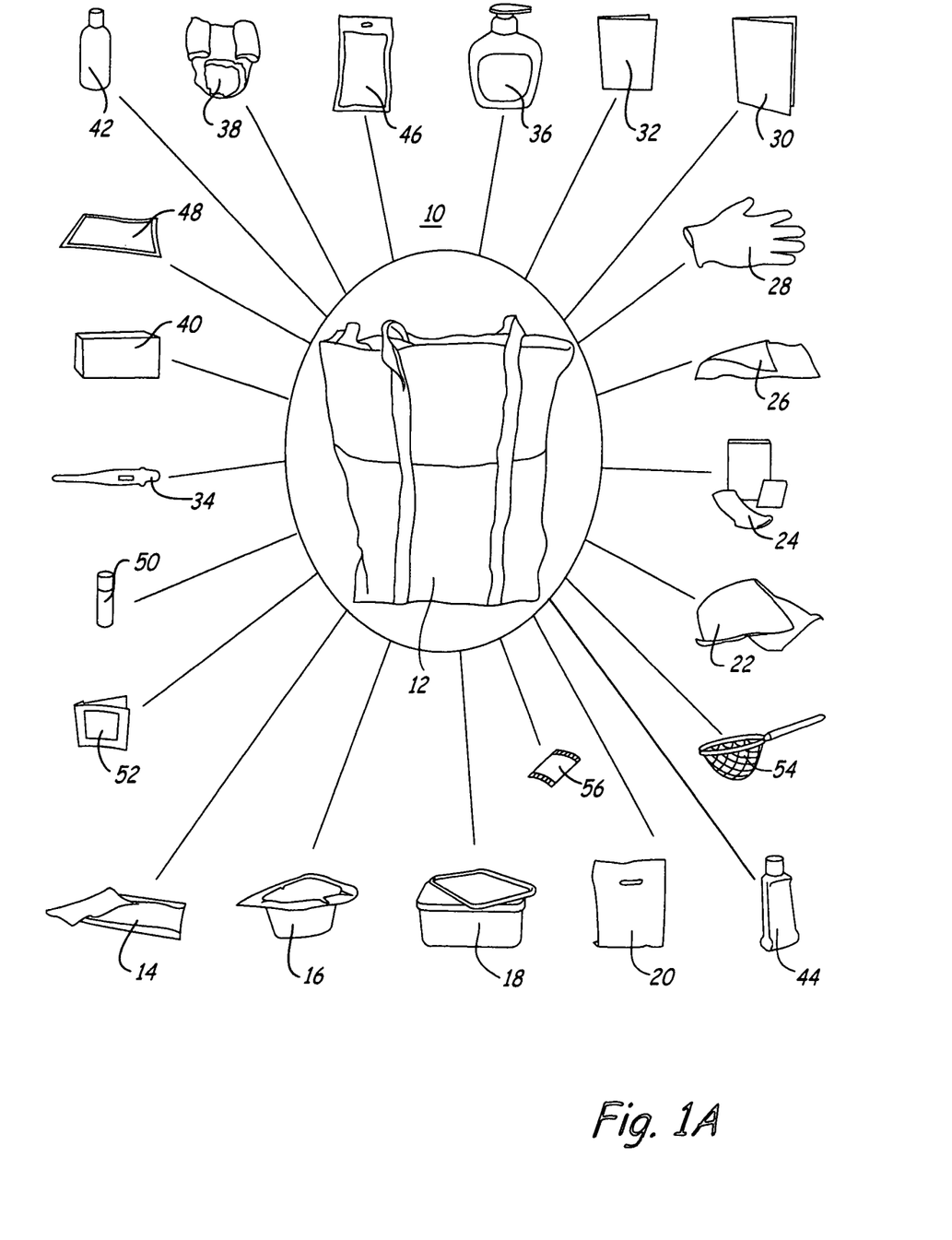
FIG. 1A is a diagrammatical representation of the invention, the miscarriage care package.

FIG. 1A is a diagrammatical representation of the invention, the miscarriage care package 10. The package 10 is intended for use by hospitals, clinics, pharmacies, or any outlet that chooses to offer and provide a means of support and assistance to women who may experience a miscarriage, whether in or outside a medical facility or environment.

The contents of the miscarriage carriage package 10 are provided to assist a woman before, during, and after the process of miscarriage, which is typically a medical situation for which she is unlikely to have had training or experience. With the package 10, a woman is better equipped and prepared for the pending physical and emotional experience. Increased preparedness can positively impact a woman's physical and emotional recovery after a miscarriage. Additionally, increased preparedness can foster a positive bond between the woman and her physician and clinic, because the package 10 conveys a message of concern, compassion, and respect.

In one embodiment, as illustrated in FIG. 1A, the package 10 will include a carrying case 12 (e.g., a tote, a bag, a handled case, a box, etc.) that contains underpad/bed-liners 14, a specimen pan 16, a pregnancy remains container 18, a biohazard safety or container bag 20, large sanitary napkins 22, small sanitary napkins 24, disposable towels 26, disposable gloves 28, an information booklet 30, and a comfort/encouragement card 32. In one embodiment, the carrying case 12 will also contain a thermometer 34, antibacterial soap 36, protective undergarments 38, pain management medication 40 (e.g., ibuprofen, acetaminophen, etc.), massage oil 42, blood stain remover 44, reusable disposable towels 46, a therapeutic hot/cold pack 48, lip balm 50, announcement cards 52, a strainer 54, and antibacterial wipes 56.

The listing of the aforementioned items is not exhaustive and those skilled in the art will realize that other useful items besides those listed above may be included in the package 10 without departing from the spirit of the invention. Also, different embodiments of the invention will include different combinations of the aforementioned items, and the items may be provided in one or more carrying cases 12.

In one embodiment, the package 10 is designed to look innocuous. In one embodiment, the carrying case 12 will be designed so that a woman leaving her clinic, hospital, store or other facility with the package 10 will appear as though she is carrying nothing more than an unassuming bag or tote 12. The bag 12 will be designed to be large enough to contain the necessary items. In another embodiment, the carrying case 12 will be a box, brief case, or any other container/transport device that can be used to carry and conceal the contents of the package 10. In other embodiments, the container 12 is less innocuous and offers less concealment of the contents, but is still adequate to carry some or all of the items comprising the package 10.

All of the items comprising the package 10, including the tote 12, are meant to be disposable. Should the woman not need, or choose not to use the items, they may be removed from the bag 12 at anytime. The contents and packaging of the package 10 are intended to be disposable so as to eliminate any lingering artifacts of the miscarriage. A miscarriage leaves emotional scars due to the trauma experienced by the body and psyche. Thus, concrete reminders of the event may cause re-traumatization.

Figure 1B:
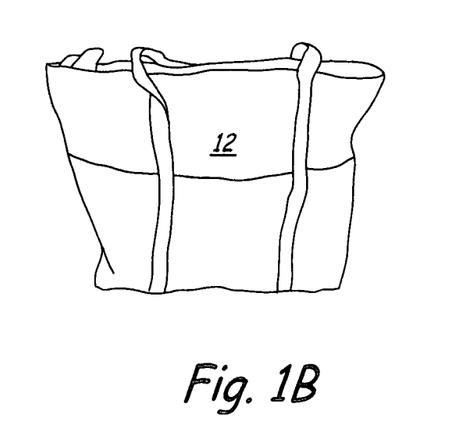
FIG. 1B is a side elevation view of a bag utilized to hold the items comprising the miscarriage care package.

In one embodiment, the miscarriage care package 10 may be packaged in a tote bag or carrying case 12 that may be constructed of any material sufficiently strong and durable to support the items contained therein. Also, the bag 12 may be of any color and may be of any size and configuration as long as it allows sufficient volume to contain the items that comprise the package 10.

In one embodiment, as shown in FIG. 1B, the bag 12 is made from 70D Nylon with PVC backing and is configured to be 23" wide×15" high and to have an 8" bottom gusset. If extra volume is needed, the tote bag 12 is adapted to expand to a height of 20" via a top zipper closure and an expandable section that provides the extra 5" in height. The bag 12 has three open pockets on one side, a vinyl covered cardboard base in the bottom of the bag 12, and shoulder length handles that are reinforced for additional strength. The bag 12 is gray in color and is offered by R-BAG Company at http://www.r-bag.com. In other embodiments, the carrying case or tote bag 12 may be made of different materials and may have different configurations, sizes, colors and features.

The bag 12 is used to house or contain the items of the package 10. The bag 12 allows a convenient and discreet means to transport the items contained therein.

A description of the items that may be contained in the carrying case or bag 12 will now be given. The following items are given as examples, and the miscarriage care package 10 may have any combination of the following items (or other useful items not listed) and still remain within the spirit of the invention.

Figure 2:
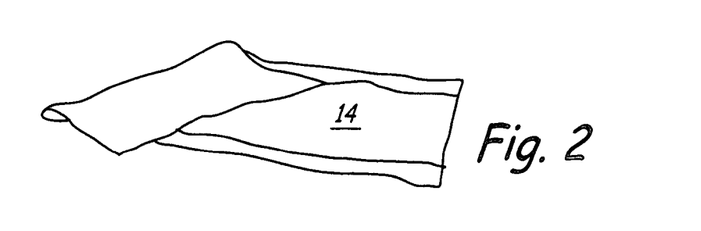
FIG. 2 is a top perspective view of an underpad/bed-liner that may be offered as part of the miscarriage care package and contained in the bag depicted in FIG. 1B.

In one embodiment, the package 10 contains underpad/bed-liners 14 as depicted in FIG. 2. The bed-liners 14 may vary in material, size, shape, color and absorbency. In one embodiment, the bed-liner 14 is a disposable underpad/bed-liner that is 23"×36". The bed-liner 14 has a latex free pad backing. The pad backing is made from a thick polypropylene and has a non-skid feature to ensure the product stays in place. The bed-liner 14 has an absorbent padding that is adhered to one side of the backing. This absorbent padding is centered onto the backing with a 1.5" frame surrounding the pad. In one embodiment, the disposable underpad/bed-liner 14 is mint green with a white absorbent pad and is offered by First Quality Products, Inc. of McElhattan, Pa.

In one embodiment, the miscarriage care package 10 will include a quantity of fifteen underpads/bed-liners 14. In other embodiments, the package 10 will have a greater or lesser number of underpads/bed-liners 14. The underpads/bed-liners 14 may be used in any number of ways and in any manner in which the woman or caregiver feels helpful, but is intended to assist in keeping the woman's surroundings sanitary by absorbing bodily fluids. For example, the underpad/bed-liners 14 are useful where a woman chooses to miscarry in a bed, chair, sofa or other physical surroundings. The bed-liner 14 helps to reduce worries about blood or fluid soaked bedding or fabrics and the discomfort of washing or cleaning these after miscarriage.

Figure 3A:
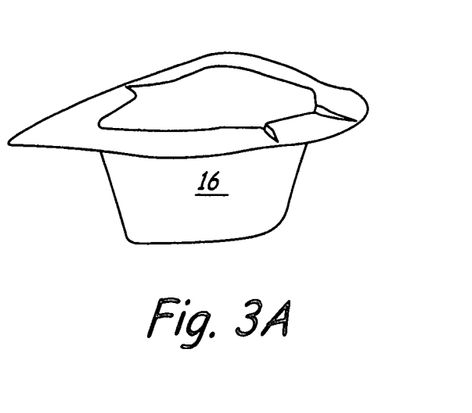
FIG. 3A is a top perspective view of a specimen pan that may be offered as part of the miscarriage care package and contained in the bag depicted in FIG. 1B.
Figure 3B:
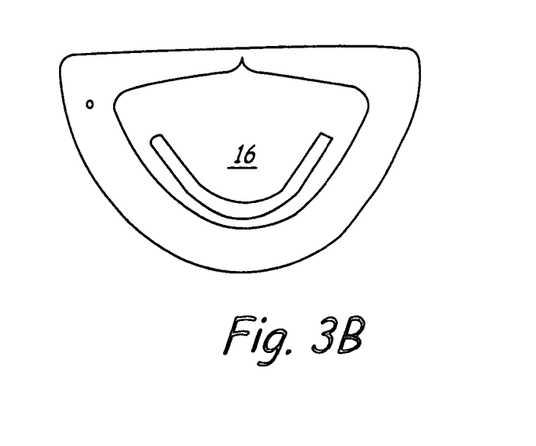
FIG. 3B is a top view of the specimen pan shown in FIG. 3A.

In one embodiment, the package 10 contains a specimen pan 16 as shown in FIGS. 3A and 3B. The specimen pan 16 is made from a durable material (e.g., plastic, rubber or metal) and is shaped to fit inside the rim of a standard toilet.

In one embodiment, the pan 16 has a triangular top configured to allow the pan 16 to fit atop the toilet rim. The pan 16 is approximately 12.5" wide×8" long×4" deep. In one embodiment, the pan 16 has an incline labeled with a measurement guide having measurement increments ranging up to 32 ounces or 1000 cubic centimeters. The pan 16 is offered by Duro-Med Industries of Jesup, Ga. In other embodiments, the pan 16 will have other shapes, sizes and features and will be made of other materials.

The specimen pan 16 assists in collecting and/or calculating blood or other bodily fluid loss for recording purposes. Fluid loss must be monitored and recorded to determine whether safe limits have been exceeded. The specimen pan 16 can also be used to collect tissue and/or fetal remains, sparing the additional trauma of retrieving fetal remains from an unsanitary toilet. Once the bodily fluids, tissue and/or fetal remains are collected in the pan 16, they may be transferred to a spill-proof, sanitary container, such as the pregnancy remains container 18 depicted in FIG. 4, which is another item that may be provided in the miscarriage package 10.

Figure 4:
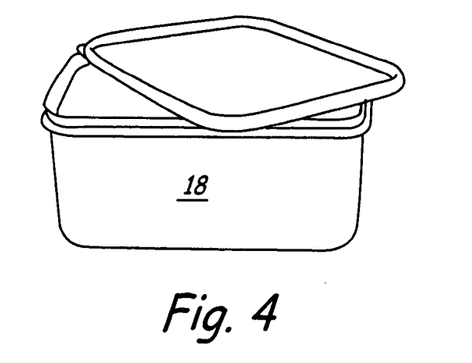
FIG. 4 is a top perspective view of a pregnancy remains container that may be offered as part of the miscarriage care package and contained in the bag depicted in FIG. 1B.

In one embodiment, as shown in FIG. 4, the pregnancy remains container 18 is rectangular in shape, is approximately 6.5" long×5" wide×3.75" deep, will hold up to 60 ounces of fluids, is made from opaque polyurethane plastic, has a snap-on, spill-proof lid, and is labeled with biohazard indicators. The container 18 is offered by United States Plastic Corporation of Lima, Ohio.

In other embodiments, the container 18 will be made of other materials and will have other configurations, sizes and capacities based on what is deemed appropriate for the stage of pregnancy ending in miscarriage. The container 18 is used to hold and transport any bodily fluids, tissue or fetal remains until they can be analyzed/examined, transported, permanently stored, or properly disposed.

Figure 5:
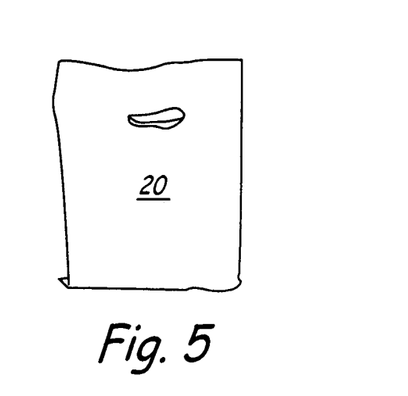
FIG. 5 is a side elevation view of a biohazard safe bag or container bag that may be offered as part of the miscarriage care package and contained in the bag depicted in FIG. 1B.

In one embodiment, the package 10 contains one or more biohazard safe bags 20 (i.e., container bags) as depicted in FIG. 5. In one embodiment, as shown in FIG. 5, the biohazard safe bag 20 has a handle. In other embodiments, the bag 20 does not have a handle. In one embodiment, the bag 20 is sealed shut via a twist tie. In other embodiments, the bag 20 is sealed shut via a ZIPLOCK® type, zipper means. The biohazard safe or container bag 20 is used to carry the pregnancy remains container 18 and has a volume and strength that is sufficient to accommodate the container 18 and its contents. The bag 20 acts as additional, outside packaging to further protect and disguise the container 18 and pregnancy remains in the event they are transported to a medical facility or funeral home. In other embodiments, the bag 20 will have other sizes, capacities, shapes, and features and will be made of other materials. The biohazard safe bag 20 is offered by R-BAG Company at http://www.rbag.com.

Figure 6:
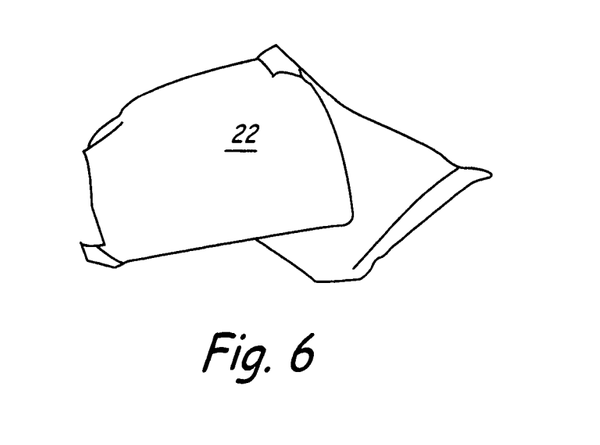
FIG. 6 is a top perspective view of a large sanitary napkin that may be offered as part of the miscarriage care package and contained in the bag depicted in FIG. 1B.

In one embodiment, the miscarriage care package 10 contains twelve large sanitary napkins 22 as depicted in FIG. 6. In one embodiment, the large sanitary napkins 22 are made of a high absorbency, disposable material and will be approximately 8" wide×21" long. The large sanitary napkins 22 are backed with plastic and have two adhesive strips on the backside to allow for proper placement in undergarments. The large sanitary napkins 22 may vary in design, material, size and shape. Also, the number of large sanitary napkins 22 provided in the package 10 will vary depending on the needs of the patient. The large sanitary napkins 22 are worn closest to the body and are used to absorb, control, and/or contain body fluids during and as needed after miscarriage. The large sanitary napkins 22 are offered by Tranzonic Companies of Cleveland, Ohio.

Figure 7:
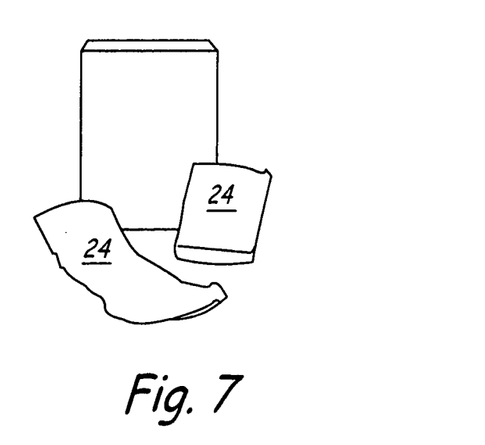
FIG. 7 is a top perspective view of small sanitary napkins and their packaging box, which may be offered as part of the miscarriage care package and contained in the bag depicted in FIG. 1B.

In one embodiment, the miscarriage care package 10 contains twelve small sanitary napkins 24 as shown in FIG. 7. In one embodiment, the small sanitary napkins 24 are individually packaged in a box and have an absorbency that is high, but less than that of the large sanitary napkins 22. The small sanitary napkins 24 are disposable and are approximately 3" wide×10" long. The small sanitary napkins 24 are backed with plastic and have one adhesive strip on the backside to allow for proper placement in undergarments. The small sanitary napkins 24 may vary in design, material, size and shape. Also, the number of small sanitary napkins 24 provided in the package 10 will depend on the needs of the patient. The small sanitary napkins 24 are worn closest to the body and are used to provide discrete, convenient protection from bodily fluids before, during, or after miscarriage. The small sanitary napkins 24 are offered by Tranzonic Companies of Cleveland, Ohio.

The large and small sanitary napkins 22, 24 are of use because a woman will continue to bleed for approximately 14 days after miscarriage. During this time period, tampon use is usually medically not recommended in favor of sanitary napkins.

Figure 8:
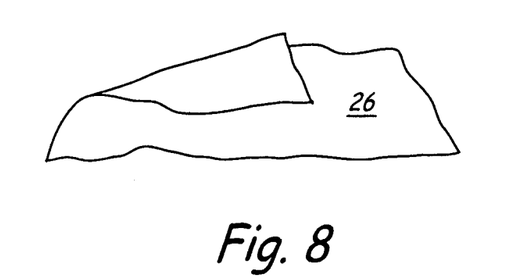
FIG. 8 is a top perspective view of a disposable towel that may be offered as part of the miscarriage care package and contained in the bag depicted in FIG. 1B.

In one embodiment, the miscarriage care package 10 contains twelve disposable towels 26 as depicted in FIG. 8. In one embodiment, the towels 26 are textured one-ply paper products that are 12.5" wide×14" long. In other embodiments, the towels 26 may be of a different ply, material, shape, and/or size. Also, in other embodiments, a greater or lesser number of towels 26 will be provided in each package 10. The disposable towels 26 are used to aid in absorbing, containing, removing and sanitizing bodily fluids from surfaces and materials during and after the miscarriage.

Figure 9:
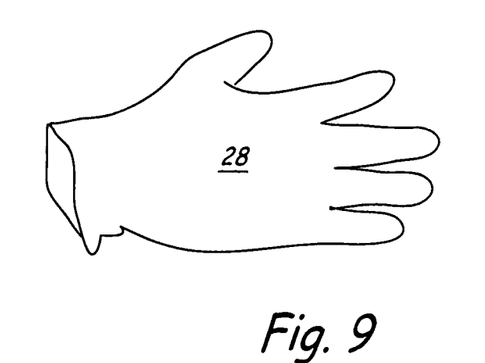
FIG. 9 is a top perspective view of a disposable glove that may be offered as part of the miscarriage care package and contained in the bag depicted in FIG. 1B.

In one embodiment, the miscarriage care package 10 contains six disposable gloves 28 as shown in FIG. 9. In other embodiments, a greater or lesser number of gloves 28 is provided. In one embodiment, the gloves 28 are a large size, made from a latex-free vinyl, and are an opaque yellow in color. In other embodiments, the gloves 28 may be other sizes, colors, and made from other materials. In one embodiment, the gloves 28 are sterile. In another embodiment, the gloves 28 are non-sterile. The gloves 28 are offered by Maxxim Medical, Inc. of Waltham, Mass. The gloves 28 offer protection to the caregiver as needed during or after the miscarriage. The gloves 28 also can help during cleanup and can help protect the woman against infection.

Figure 10:
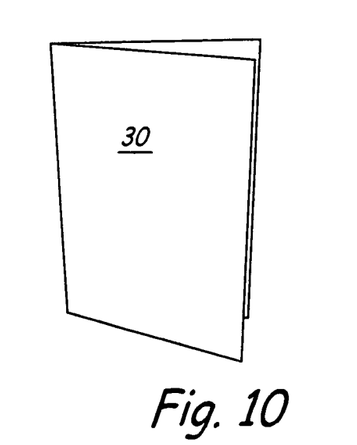
FIG. 10 is a top perspective view of an information booklet that may be offered as part of the miscarriage care package and contained in the bag depicted in FIG. 1B.

In one embodiment, the miscarriage care package 10 contains an information booklet 30 as depicted in FIG. 10. In one embodiment, the booklet 30 has a half-page, saddle-stitch design and contains medical, emotional, and practical information. The booklet 30 includes a checklist for medical professionals to document contact with the patient and a chart to record the physical progression of the miscarriage. The booklet 30 also includes a page for recording addresses and telephone numbers for local and national support resources that may be contacted before, during and/or after a miscarriage. The booklet 30 includes instructions to guide a woman or her caregiver on whom to contact to arrange for the disposal of the fetal remains, tissue or fluids. Finally, the booklet 30 describes the natural process of miscarriage and contains guidelines, data, and suggestions appropriate to the experience of miscarriage whether before, during, or after the event. In other embodiments, the booklet 30 will have additional or other features and will have other sizes and designs.

By studying the booklet 30, no woman, or couple, should be unprepared when a pregnancy ends in miscarriage. The booklet 30 guides the woman through the miscarriage process and provides the necessary medical and psychological information. The booklet 30 is written in a straightforward manner and is presented in an easy-to-read format. The booklet 30 is intended to arm a woman with the knowledge she needs to better deal with her pregnancy loss and its aftermath. Having this information during miscarriage can ease the shock, pain, fear and emotional devastation experienced when a woman is under prepared for a miscarriage. The booklet 30 is offered by WomenCare of Wayzata, Minn.

Figure 11:
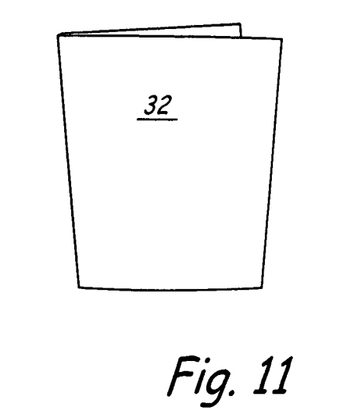
FIG. 11 is a top perspective view of a comfort/encouragement card that may be offered as part of the miscarriage care package and contained in the bag depicted in FIG. 1B.

In one embodiment, the miscarriage care package 10 contains a comfort/encouragement card 32 as shown in FIG. 11. In one embodiment, the card 32 is printed on heavy weight card stock of at least 65 pounds. In other embodiments, the card 32 is printed on other types of card stock or materials. The card 32 may have any number of images, messages, and/or enclosures. The card 32 is meant to covey a heartfelt message of support to a woman from her medical caregiver and allows the caregiver to convey compassion and support to women who are in receipt of the miscarriage care package 10. Once signed and given to the woman, she can appreciate that the medical caregiver cares about her physical and emotional state. The comfort/encouragement card 32 is offered by WomenCare of Wayzata, Minn.

Figure 12:
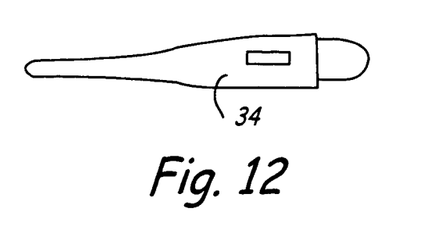
FIG. 12 is a top perspective view of a thermometer that may be offered as part of the miscarriage care package and contained in the bag depicted in FIG. 1B.

In one embodiment, the miscarriage care package 10 contains a thermometer 34 as depicted in FIG. 12. In one embodiment, the thermometer 34 is a digital read thermometer that operates on a 15V battery. The thermometer 34 is 4.5" long and is silver in color. The main structure is made from a hard waterproof plastic. The thermometer 34 has a clear plastic storage case. The digital display is a graphite color. The thermometer 34 provides a reading in 60 seconds and is accurate within +/−0.2 F°. The memory recall feature will display the last temperature taken. The thermometer 34 has an automatic shut-off feature to prolong battery life. The on/off feature is located near the end of the unit and is activated by pressing in the switch. The thermometer 34 is completely waterproof and may be used orally or rectally. In one embodiment, the thermometer 34 is a model 820 offered by KAZ, Inc. of Hudson, N.Y. In other embodiments, the thermometer 34 will have other features, sizes, and configurations.

In one embodiment, the thermometer 34 is disposable. This type of thermometer adheres to the patient's forehead or an appropriate location on the body to continually track the patient's temperature. The thermometers are used to track any change in body temperature, which may be an indication of infection.

Figure 13:
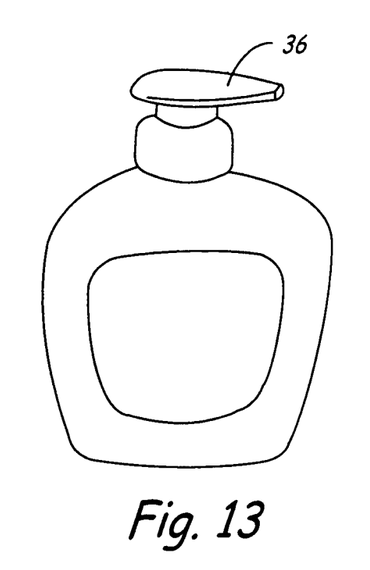
FIG. 13 is a top perspective view of a container of antibacterial soap that may be offered as part of the miscarriage care package and contained in the bag depicted in FIG. 1B.

In one embodiment, the miscarriage care package 10 contains antibacterial soap 36 as depicted in FIG. 13. In one embodiment, the antibacterial soap 36 is a single container of two fluid oz. (59 ml). In other embodiments, greater or lesser amounts of antibacterial soap are provided in each package 10.

The antibacterial soap 36 is dermatology tested and hypoallergenic. The active ingredients, size, color and contents of the antibacterial soap 36 may vary depending on the embodiment. Also, depending on the embodiment, the antibacterial soap 36 may or may not contain a light moisturizer. The soap 36 may be used for hand and body cleansing as well as general cleaning of tile, porcelain, countertops, stainless steel, or any surface in which bodily fluids may come in contact.

In one embodiment, the active ingredients of the antibacterial soap 36 include triclosan, while other ingredients include: water; sodium laureth sulfate; cocamidpropyl; betaine; sodium chloride; decyl glucoside; fragrance; DMDM hydantoin; peg 120 methyl; glucose dioleate; tetrasodium; edta; citric acid; sodium sulfate; polyquaternium 7; poloxamer 124; and peg 7 glyceryl cocoate. The soap 36 is offered by Colgate-Palmolive Company of New York, N.Y.

The antibacterial soap 36 is utilized for cleaning and to kill germs transferred through contact with the bodily fluids expelled during the miscarriage process. The antibacterial soap 36 is effective in killing germs on both surfaces and persons.

Figure 14:
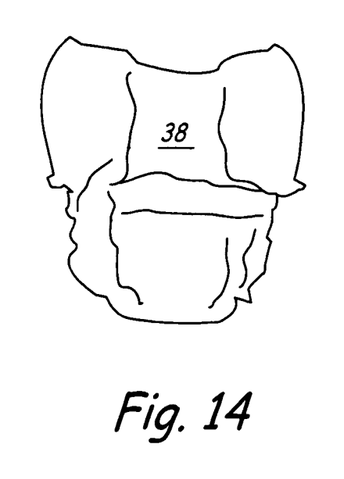
FIG. 14 is a front view of a protective undergarment that may be offered as part of the miscarriage care package and contained in the bag depicted in FIG. 1B.

In one embodiment, the miscarriage care package 10 contains protective undergarments 38 as shown in FIG. 14. In one embodiment, the package 10 provides twelve protective undergarments 38. In other embodiments, a greater or lesser number of undergarments 38 are provided.

The undergarments 38 may be offered in various colors, materials, shapes, textures, weights, features and sizes. In one embodiment, the undergarments 38 are made of a high absorbency, lightweight material and are comfortable to a woman's skin. In one embodiment, the undergarments 38 have a soft, cloth-like moisture barrier panty with a form fitting elastic waistband and leg openings. The undergarments 38 contain an extremely absorbent core that gives protection where it is most needed.

The leg openings of the undergarments 38 have flexible gathers that offer a secure fit to prevent leakage due to heavy blood flow. The undergarments 38 are easily removed by tear away sides. The undergarments 38 may be worn throughout the day or night for maximum protection against bodily fluid leakage.

The undergarments 38 come in various sizes that are configured to accommodate various waist and hip sizes. In one embodiment, the package 10 contains undergarments 38 that are appropriately sized for the woman receiving the package 10. The undergarments 38 are offered by Target Corporation of Minneapolis, Minn. The undergarments 38 are used to absorb and/or contain bodily fluids prior to, during, and as needed after miscarriage.

Figure 15:
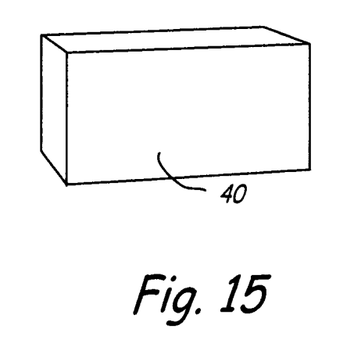
FIG. 15 is a top perspective view of a package of pain management medication that may be offered as part of the miscarriage care package and contained in the bag depicted in FIG. 1B.

In one embodiment, the miscarriage care package 10 contains a package of pain management medication 40 (e.g., ibuprofen, acetaminophen, aspirin, etc.) as depicted in FIG. 15. In one embodiment, the medication 40 may be offered in a tablet, capsule, coated tablet, chewable or liquid form. The capsule or coating may vary in color or material.

In one embodiment, the medication 40 is offered in a single container with ten doses of 200 mg strength. In other embodiments, the medication 40 is offered in greater or lesser strength and in a greater or lesser number of doses. The number of doses and the strength of the doses will depend on the direction given by the woman's clinic or physician.

The medication 40 is offered in a tamper resistant container, which may vary in color, size, and shape. In one embodiment, ibuprofen is the active ingredient in the medication 40. Ibuprofen has the following inactive ingredients: crosarmellose sodium, hydroxypropyl cellulose, hydroxypropyl methylcellulose, microcrystalline cellulose, polyethylene glycol, povidone, pregelatinized starch, red iron oxide, silicon dioxide, sodium starch glycolate, stearic acid, titanium dioxide. The ibuprofen is offered by Target Corporation of Minneapolis, Minn. After receiving authorization from their attending physician, the woman may utilize the medication 40 to manage the cramping and contraction pain that occurs throughout the miscarriage process.

Figure 16:
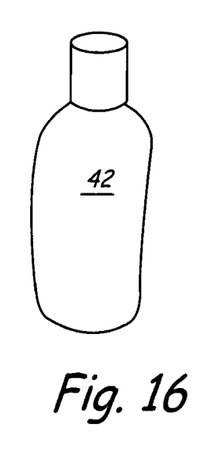
FIG. 16 is a top perspective view of a bottle of massage oil that may be offered as part of the miscarriage care package and contained in the bag depicted in FIG. 1B.

In one embodiment, the miscarriage care package 10 contains massage oil 42 as depicted in FIG. 16. In one embodiment, the massage oil 42 is offered as a single container of eight fluid ounces. In other embodiments, the massage oil 42 may be offered in greater or lesser quantities. The massage oil 42 may be offered with or without fragrance.

In one embodiment, the massage oil 42 may have the following ingredients: sunflower oil, sweet almond oil, grape seed oil, avocado oil, sesame oil, chamomile extract, calendula extract, and tocopherol. Other embodiments will have other ingredients. Depending on the embodiment, the massage oil may or may not contain natural ingredients. In one embodiment, the massage oil is hypoallergenic.

In one embodiment, the massage oil 42 may be provided in an opaque plastic bottle with a black screw on cap. In other embodiments, the massage oil 42 will come in containers of other sizes, shapes, and colors. Also, depending on the embodiment, the massage oil 42 may be of different colors, scents, consistencies, and ingredients. The massage oil 42 is offered by Garden Botanika of Redmond, Calif. The massage oil 42 is utilized to stimulate relaxation in a woman experiencing a miscarriage. The massage oil 42 provides a means of offering supportive care to the woman.

Figure 17:
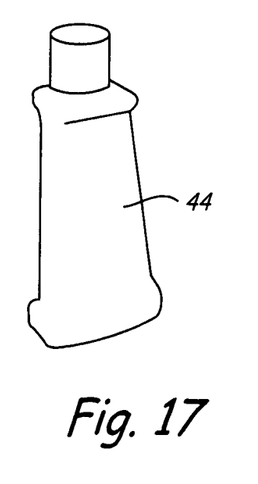
FIG. 17 is a top perspective view of a bottle of blood stain remover that may be offered as part of the miscarriage care package and contained in the bag depicted in FIG. 1B.

In one embodiment, the miscarriage care package 10 contains blood stain remover 44 as shown in FIG. 17. In one embodiment, the blood stain remover 44 is provided in a single, child-resistant container of 1.7 ounces. The blood stain remover 44 contains ingredients that will remove protein based stains from machine washable garments. The blood stain remover 44 is offered by Carbona Products of Fairfield, N.J. The blood stain remover 44 assists the woman or caregiver in removing blood fluid or tissue stains on washable fabrics, including linens, towels, undergarments, clothing, and carpeting.

Figure 18:
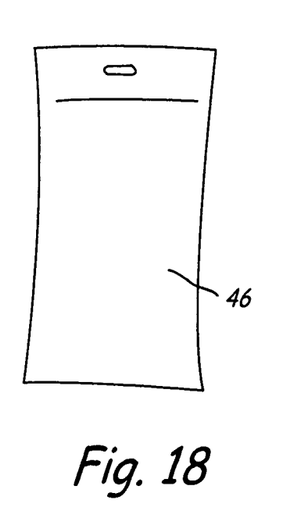
FIG. 18 is a front view of a package of reusable disposable towels that may be offered as part of the miscarriage care package and contained in the bag depicted in FIG. 1B.

In one embodiment, the miscarriage care package 10 contains reusable disposable towels 46 as depicted in FIG. 18. In one embodiment, the reusable disposable towels 46 are made of a heavyweight, non-woven material that is light and durable. In one embodiment, a single package of five towels 46 will be included. In other embodiments, the miscarriage care package 10 will contain more or less than five towels 46.

The towels 48 are strong enough to be rinsed/washed and reused if needed. In one embodiment, the towels 48 are constructed of a man-made fiber that is textured for better scrubbing power. In one embodiment, the towels 48 have a 17"×19" area and have a white and royal blue stripe pattern. The reusable disposable towels 46 are offered by Helmac Products Corporation of Alpharetta, Ga. In other embodiments, the towels 46 will have other sizes, shapes, and designs and be made of other materials. The towels 46 assist the woman or caregiver in cleaning blood, bodily fluids, or tissue that is expelled during a miscarriage.

Figure 19:
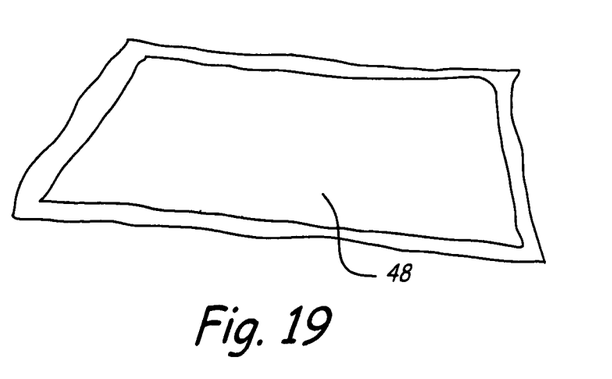
FIG. 19 is a top perspective view of a reusable therapeutic hot/cold pack that may be offered as part of the miscarriage care package and contained in the bag depicted in FIG. 1B.

In one embodiment, the miscarriage care package 10 contains a reusable therapeutic hot/cold pack 48 as shown in FIG. 19. In one embodiment, the pack 48 is 10"×15" in size and consists of a blue gel enclosed in a heavy-duty clear plastic casing. In other embodiments, the pack 48 may be of a different size, design and configuration and the package 10 may contain more than one pack 48. In one embodiment, an instruction sheet with photos directs the user in safe handling and heating of the pack 48. The pack 48 is offered by Bird & Cronin, Inc. of Egan, Minn. The pack 48 is used to provide warm comfort to a woman experiencing uterine cramps or contractions during the miscarriage process.

Figure 20:
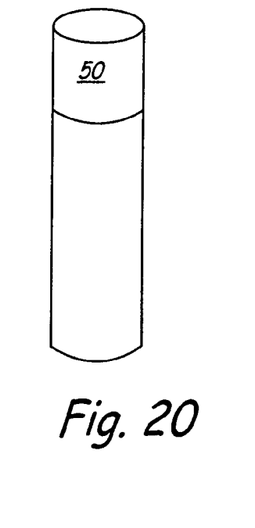
FIG. 20 is a top perspective view of a container of lip balm that may be offered as part of the miscarriage care package and contained in the bag depicted in FIG. 1B.

In one embodiment, the miscarriage care package 10 contains lip balm 50 as depicted in FIG. 20. In one embodiment, the lip balm 50 comes in a 1.5 ounce container and includes the following active ingredients: dimethicone; oxybenzone; and padimate. The lip balm 50 that is offered by Blistex of Oakbrook, Ill. In other embodiments, the lip balm 50 will have different ingredients and come in other sizes. The lip balm 50 provides healing and protective moisture to a woman's lips throughout the miscarriage process.

Figure 21:
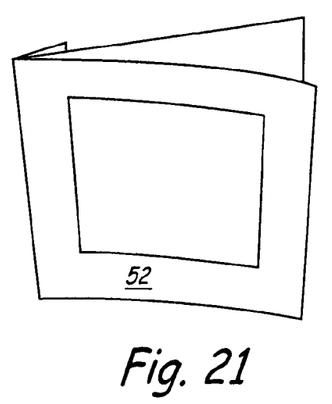
FIG. 21 is a top perspective view of an announcement card that may be offered as part of the miscarriage care package and contained in the bag depicted in FIG. 1B.

In one embodiment, the miscarriage care package 10 contains twelve announcement cards 52 as shown in FIG. 21. In other embodiments, the package 10 will contain a greater or lesser number of cards 52. In one embodiment, the package 10 contains instructions for ordering additional cards 52. In one embodiment, the cards 52 are printed on medium weight card stock. In other embodiments, the cards 52 are printed on other types of card stock or materials. The cards 52 may have any number of images, messages, and/or enclosures and are provided with mailing envelopes. In one embodiment, the cards 52 are replicas of the comfort/encouragement card 32. The cards 52 are used to notify family, friends and others of the miscarriage. The cards 52 are offered by WomenCare of Wayzata, Minn.

Figure 22:
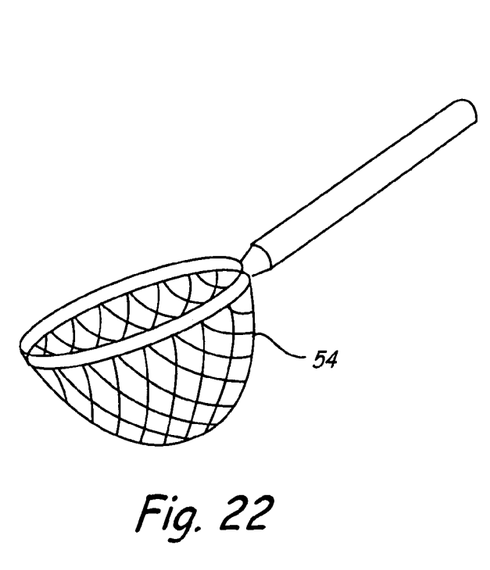
FIG. 22 is a top perspective view of a strainer that may be offered as part of the miscarriage care package and contained in the bag depicted in FIG. 1B.

In one embodiment, the miscarriage care package 10 contains a strainer 54 as depicted in FIG. 22. In one embodiment, the strainer is four inches in diameter and one and a half inches in depth. In one embodiment, it has two handles. One handle is five inches in length and the other handle is one inch in length. In one embodiment, the strainer is completely stainless steel and has medium density mesh. In other embodiments, the strainer 54 has a greater or lesser number of handles, a larger or smaller diameter and depth, and a mesh that is fine, medium, or coarse and made of plastic or metal.

The strainer 54 is used to separate the fetal or pregnancy remains from other bodily fluids or watery liquids. The strainer 54 is offered by Fox Fun Crafts of Ivyland, Pa.

Figure 23:
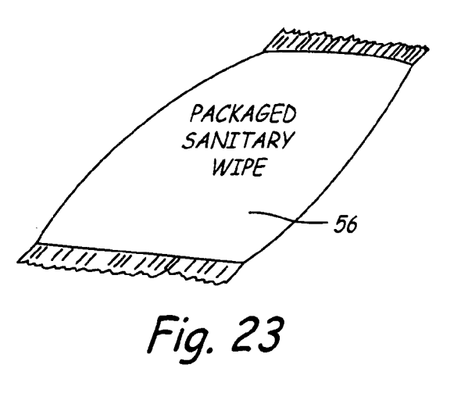
FIG. 23 is a top perspective view of an individually packaged antibacterial wipe that may be offered as part of the miscarriage care package and contained in the bag depicted in FIG. 1B.

In one embodiment, the miscarriage care package 10 contains ten individually packaged antibacterial wipes 56 (or sanitizing hand towels) as shown in FIG. 23. In other embodiments, the package 10 contains a greater or lesser number of wipes 56. The wipes 56 are used to clean and sanitize surfaces that have encountered body fluids or tissue expelled during a miscarriage.

In one embodiment, the wipes 56 are 5"×7.5" in size. They are package in a sealed white foil pouch with a notched indentation for ease of opening. The pouch is 3"×2⅜" in size. In one embodiment, the wipes 56 contain moisturizer, vitamins A & E, and Aloe. In other embodiments, the wipes 56 are different sizes, are made of different materials, and contain different ingredients. The wipes 56 are offered by Gojo Industries, Inc. Akron, Ohio.

As previously stated, the aforementioned items do not comprise an exhaustive list of the useful items that could be included in the miscarriage care package 10. Those skilled in the art will realize that other useful items besides the aforementioned items may be included in the package 10 without departing from the spirit of the invention.

Depending on the needs of the patient (e.g., the pregnancy stage when the miscarriage occurs, where the miscarriage will occur, the patient's emotional an/or physical state, etc.) and economic considerations (e.g., the costs of the individual items and the total cost of the package 10), different embodiments of the package 10 will include different combinations of the aforementioned items. Depending on the number of items provided and their types and sizes, the items may be provided in one or more carrying cases 12.

In one embodiment, the package 10 is provided without a dedicated carrying case 12, the items being provided individually or provided within another item. For example, the smaller items are rolled/folded up within the underpad/bedliners 14 or placed within the pregnancy remains container 18 and/or the specimen pan 16.

The miscarriage care package 10 will, in one embodiment, be utilized as follows. A medical services provider (e.g., physician, nurse, clinic, hospital, etc.) examines a woman and determines that her pregnancy is ending, likely to end, or has ended in miscarriage. The medical services provider considers the woman's pregnancy stage and her physical and emotional condition and provides her with a miscarriage care package 10 comprising some or all of the aforementioned items. In another embodiment, after determining the pregnancy is likely to end in miscarriage and after considering her needs and pregnancy stage, the medical services provider provides the woman with a list reciting some or all of the aforementioned items. The woman (or another) then follows the list and obtains the items in preparation for the miscarriage.

In one embodiment, the woman and/or her caregiver (i.e., a medical professional and/or the woman's partner, relative, friend, etc.) utilize the miscarriage care package 10 in a medical facility (e.g., clinic or hospital). In one embodiment, the woman and/or her caregiver utilize the miscarriage care package 10 outside a medical facility (e.g., in the privacy of the woman's residential home or that of a close family member).

Although the present invention has been described with reference to preferred embodiments, persons skilled in the art will recognize that changes may be made in form and detail without departing from the spirit and scope of the invention.

We claim:

1. A miscarriage kit comprising:
   at least one under pad/bed liner configured to be positioned on a surface, the under pad/bed liner having a bottom layer and a top layer, wherein the top layer is designed to absorb bodily fluids, and wherein the bottom layer protects the surface from bodily fluids that soak through the top layer;
   at least one sanitary napkin;
   at least one towel;
   at least one pair of gloves;
   at least one specimen pan for receiving human tissue; and
   at least one container for holding fetal remains for legal disposition.

2. The kit of claim 1, wherein the container for holding pregnancy remains is a spill-proof, sanitary container.

3. The kit of claim 1, further comprising a list of one or more items for use in helping the human in at least one of managing, controlling, cleaning up, handling, acquiring samples of, and disposing of the body fluids discharged before, during, or after a miscarriage based on the human's going through a miscarriage.

4. The kit of claim 1, further comprising one or more items used in helping the human in at least one of managing, controlling, cleaning up, handling, acquiring samples of, and disposing of the body fluids discharged before, during, or after a miscarriage based on the human's going through a miscarriage.

5. The kit of claim 1, further comprising one or more items used in helping the human in at least one of managing, controlling, cleaning up, handling, acquiring samples of, and disposing of the body fluids discharged before the human experiences a miscarriage.

6. The kit of claim 1, further comprising one or more items used in helping the human in at least one of managing, controlling, cleaning up, handling, acquiring samples of, and disposing of the body fluids discharged substantially during the period the human experiences a miscarriage.

7. The kit of claim 1, further comprising one or more items used in helping the human in at least one of managing, controlling, cleaning up, handling, acquiring samples of, and disposing of the body fluids discharged after the miscarriage.

8. The kit of claim 1, wherein the human tissue comprises fetal remains.

9. The kit of claim 1, wherein the under pad/bed liner comprises an absorbent padding on the top surface and an impermeable backing on the bottom surface.

10. A miscarriage kit comprising:
    at least one under pad/bed liner configured to be positioned on a surface, the under pad/bed liner having a bottom layer and a top layer, the top layer is designed to absorb bodily fluids, and wherein the bottom layer protects the surface from bodily fluids that soak through the top layer;
    at least one sanitary napkin;
    at least one towel;
    at least one pair of gloves;
    at least one specimen pan, wherein the specimen pan is configured to fit inside the rim of a toilet and further includes an upper rim configured to allow the upper rim to rest atop the toilet rim, the specimen pan having an opening positioned and sized to receive fluids and human tissue from a miscarriage, and wherein the specimen pan is comprised of a durable material; and
    wherein the specimen pan provides a measurement guide for measurement of fluid loss; and
    at least one container for holding fetal remains for legal disposition, wherein the container is opaque.

11. The miscarriage kit of claim 10, wherein the measurement guide allows the woman to measure fluid loss to assist her doctor in diagnosing a hemorrhage.

12. The miscarriage kit of claim 10, wherein the measurement guide shows one or more of the following measurements in any combination
   fluid ounces;
   cubic centimeters (cc).

13. A miscarriage kit comprising:
   at least one under pad/bed liner;
   at least one sanitary napkin;
   at least one towel;
   at least one pair of gloves;
   at least one specimen pan for receiving human tissue; and
   at least one container for holding fetal remains for legal disposition; and
   at least one thermometer.

14. The miscarriage kit of claim 13, further comprising at least one protective undergarment.

15. The miscarriage kit of claim 1, wherein the bottom layer of the under pad/bed liner is impermeable to bodily fluids.

16. The miscarriage kit of claim 1, wherein the bottom layer of the under pad/bed liner is polypropylene.

17. The miscarriage kit of claim 1, wherein the under pad/bed liner further comprises a non-skid feature.

\* \* \* \* \*